United States Patent
Rasmussen et al.

(10) Patent No.: US 6,379,952 B1
(45) Date of Patent: Apr. 30, 2002

(54) METHOD FOR CELL SELECTION UTILIZING AZLACTONE-FUNCTIONAL SUPPORTS

(75) Inventors: Jerald K. Rasmussen, Stillwater; Patrick L. Coleman, Minneapolis, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/240,829

(22) Filed: Feb. 1, 1999

(51) Int. Cl.[7] .............................. C12N 5/06; C12N 5/08; C12N 11/08; C12N 11/06; C07K 17/08
(52) U.S. Cl. ..................... 435/325; 435/180; 435/181; 435/261; 435/372; 435/395; 530/413; 530/815; 530/816
(58) Field of Search .................................. 435/174, 177, 435/180, 181, 325, 372, 395, 261; 530/413, 815, 816

(56) References Cited

U.S. PATENT DOCUMENTS

| | | | |
|---|---|---|---|
| 5,013,795 A | 5/1991 | Coleman et al. | 525/279 |
| 5,035,994 A | 7/1991 | Civin | 435/2 |
| 5,200,471 A | 4/1993 | Coleman et al. | 525/326.9 |
| 5,215,927 A | 6/1993 | Berenson et al. | 436/541 |
| 5,262,484 A | 11/1993 | Coleman et al. | 525/204 |
| 5,292,514 A | 3/1994 | Capecchi et al. | 424/422 |
| 5,344,701 A | 9/1994 | Gagnon et al. | 428/304.4 |
| 5,403,902 A | 4/1995 | Heilmann et al. | 526/260 |
| 5,408,002 A | 4/1995 | Coleman et al. | 525/204 |
| 5,451,453 A | 9/1995 | Gagnon et al. | 428/305.5 |
| 5,486,358 A | 1/1996 | Coleman et al. | 424/78.23 |
| 5,510,421 A | 4/1996 | Dennison et al. | 525/204 |
| 5,561,097 A | 10/1996 | Gleason et al. | 502/402 |
| 5,993,935 A | * 11/1999 | Rasmussen et al. | 428/120 |
| 6,057,096 A | * 5/2000 | Rothschild et al. | 436/6 |

FOREIGN PATENT DOCUMENTS

| | | |
|---|---|---|
| WO | WO 92/07879 | 5/1992 |
| WO | WO 93/04576 | 3/1993 |
| WO | WO 93/06925 | 4/1993 |
| WO | WO 94/00165 | 1/1994 |
| WO | WO 94/00464 | 1/1994 |
| WO | WO 94/22918 | 10/1994 |
| WO | WO 95/32792 | 12/1995 |
| WO | WO 95/34817 | 12/1995 |

OTHER PUBLICATIONS

J. Turková, "bioaffinity chromatography," *Journal of Chromatography Library*, vol. 55, pp. 161–167 (1993).
D. C. Sherrington and P. Hodge, "Polymers in Affinity Chromatography," *Syntheses and Separations Using Functional Polymers*, pp. 265–269 (1988).

* cited by examiner

*Primary Examiner*—David M. Naff
(74) *Attorney, Agent, or Firm*—Christopher D. Gram; James A. Rogers; John H. Hornickel

(57) ABSTRACT

Azlactone-functional supports are used to provide cell selection from a mixture such as bone marrow or peripheral blood having a desired target cell population. An azlactone-functional support is derivatized by covalently coupling to the support a biologically active substance that binds the target cells. A mixture containing the target cells is contacted with the derivatized support to bind the target cells to the biologically active substance, and unbound remaining mixture is removed from the support. Bound cells may be eluted from the support to obtain purified target cells. Biologically active substances include antibodies, lectins, proteins, antigens and avidin. The biologically active substance may directly or indirectly bind cells in the mixture. Indirect binding may be through a second, intermediary biologically active substance that is bifunctional. The azlactone-functional support is provided by incorporating an azlactone moiety into a base polymer support that has been selected by prescreening base polymer supports with a cell mixture to identify a base polymer support having minimal nonspecific binding of cells in the mixture.

12 Claims, No Drawings

METHOD FOR CELL SELECTION UTILIZING AZLACTONE-FUNCTIONAL SUPPORTS

FIELD OF INVENTION

This invention relates to the use of azlactone-functional supports to provide cell selection.

BACKGROUND OF INVENTION

Rapidly expanding knowledge in the areas of molecular and cellular biology, immunology, and genetics has led to the identification and characterization of a variety of highly specialized subpopulations of cells within many types of tissues. For example, the identification of rare "stem cells" in such crucial tissues as the brain, islet cells of the pancreas, and liver have led to speculation that one day many diseased tissues may be treated by regeneration of healthy tissue following cell transplantation (Beardsley, *Scientific American*, June 1998, pp. 11–12). Such therapies have, in fact, already been achieved in areas such as cancer treatment. High doses of chemotherapy or radiation needed to destroy cancerous tissue often also destroy the patient's bone marrow and, effectively, his entire immune system. A transplant of hematopoietic stem cells, previously isolated from either marrow or peripheral blood, can rescue the patient by reconstituting the bone marrow and cells of the immune system (Donahue, et al., *Blood*, 1996, 87, pp. 1644–1653). Purified stem cells or other specific cell populations are also believed to be important for developing a variety of immunotherapies (e.g., AIDS treatments) and gene therapy.

To fuel research, and indeed clinical applications, in these and related areas, increasingly effective methods of separation and purification of various cell populations are required. Over the years, a variety of methods of cell separation/purification have been utilized. These separation techniques have depended upon various biological and biochemical, physical, or immunological characteristics of the cell population to be separated (Esser, in "Cell Separation Methods and Applications", D. Recktenwald and A. Radbruch, Eds., Marcel Dekker, NY, N.Y., 1997, pp. 1–14). Immunoaffinity-based separations have shown considerable promise in terms of providing relatively pure preparations of specific cells. U.S. Pat. No. 5,035,994 (Civin) describes the use of a solid-phase linked monoclonal antibody which binds specifically to an antigen on human pluripotent lympho-hematopoietic stem cells to separate said stem cells from a suspension of marrow or blood cells. Pope, et al., (*Bioconjugate Chem.*, 1993, 4, pp. 166–171) describe the use of bifunctional silane reagents to activate glass and cellulose solid supports. Goat anti-mouse antibodies are then covalently linked to the activated supports and the derivatized supports used to selectively deplete CD34+ or CD4+ mononuclear cells from peripheral blood samples. U.S. Pat. No. 5,215,927 (Berenson, et al.) describes the immunoselection of cells using an avidin-biotin recognition system. While these and other methods described in the art allow for selection and purification of selected cell populations, there is a continued need for new methods and materials that can provide those cell populations in improved purities and yields.

Azlactone-functional supports have been described to be quite useful for the immobilization of biologically active materials. For example, U.S. Pat. No. 5,403,902 (Heilmann, et al.) describes the preparation of particulate or beaded materials to which biomacromolecules such as proteins, antibodies, enzymes, etc. can be coupled. These materials are useful, for example, in the affinity chromatographic purification of proteins. U.S. Pat. Nos. 5,262,484, 5,292,514, 5,451,453, 5,486,358, and 5,510,421 all describe other azlactone-functional supports and materials and their uses. In none of these references has it been described or suggested that azlactone-functional supports might be useful for whole cell purification or selection.

PCT Patent Publication WO 94/00464 (Bitner et al.) describes the ability of azlactone-functional supports to separate proteinaceous materials from nonproteinaceous materials. This can be useful for separation and purification of biological materials. When the azlactone-functional support is contacted with a mixture of proteinaceous and nonproteinaceous materials, the proteinaceous materials react with and become coupled to the support, and the nonproteinaceous materials (e.g., nucleic acids) do not react with the support, but remain in solution. This publication does not describe the ability to separate whole cells from naturally-occurring biological fluids, but does disclose that the nonproteinaceous material retains biological activity for further processing after separation from the azlactone-functional support that has proteinaceous material coupled thereto.

PCT Patent Publication WO 94/22918 (Velander et al.) describes a method of derivatizing a porous support in a manner that distributes the ligand. Examples disclosed in the publication identify the covalent coupling of monoclonal antibodies and proteins for further biological separation processes.

U.S. Pat. No. 5,200,471 (Coleman et al.) describes a method of covalently coupling ligands to azlactone-functional supports, particularly with a method to increase the quality of the covalently coupled ligands, to retain high specific bound biological activity.

U.S. Pat. No. 5,561,097 (Gleason et al.) describes a method of covalently coupling small molecule ligands to azlactone-functional supports in a manner that can control the density and distribution of the ligands. This method is useful for the preparation of chromatographic supports.

SUMMARY OF INVENTION

A need exists for new materials and methods for the selection or purification of whole cells. It has now been found that azlactone-functional support materials, previously known to be useful for preparation of chromatographic supports for protein purification or for the preparation of covalently coupled ligands such as proteins, enzymes, and the like, can also serve as starting materials for the preparation of supports for whole cell selection and purification.

Briefly, one aspect of the invention provides a method for cell selection comprising the steps of (a) providing an azlactone-functional support, (b) derivatizing the azlactone-functional support with a substance that is biologically active towards a desired type of whole cell, wherein the substance is covalently coupled to the azlactone-functional support, (c) contacting the product of step (b) with a mixture containing the whole cells, (d) allowing the whole cells in the mixture to interact with and bind to the coupled biologically active substance, (e) removing a remainder of the mixture from the support, and (f) optionally, eluting the bound cells from the coupled biologically active substance to produce a purified collection of the whole cells.

"Support" means any article that is or can be made azlactone-functional. Acceptable supports for use in the present invention can vary widely within the scope of the invention. A support can be porous or nonporous, depending on preferred final use. A support can be continuous or non-continuous depending on ultimate desired usage. A support can be made of a variety of materials, including supports made of ceramic, glassy, metallic, or polymeric materials or combinations of materials. A support can be flexible or inflexible depending on ultimate desired usage.

"Azlactone-functional" means that a support has azlactone-functional groups on internal and/or external surfaces of such support. Thus, such reactive supports have an azlactone-functional group of the formula:

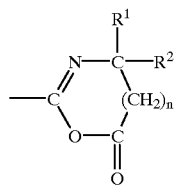

wherein:

$R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

"Covalently coupled" means chemically attached by means of a covalent bond.

"Biologically active substance" means substances which, once covalently coupled with and immobilized on the azlactone-functional support, are useful in providing selective or specific interaction with certain target whole cell populations.

"Whole cell" means a biologically active plant or animal cell that retains its structure intact during separation from other biological materials and is capable of remaining biologically active after use of the azlactone-functional support having a biologically active substance covalently coupled thereto to separate such plant or animal cell from other biological materials. Azlactone-functional supports useful for the preparation of cell selection supports include beaded or particulate supports such as those disclosed in U.S. Pat. No. 5,403,902, porous supports such as those disclosed in U.S. Pat. No. 5,344,701 and in PCT Patent Publication WO 93/06925, membrane supports such as those disclosed in U.S. Pat. No. 5,510,421, blends and articles prepared therefrom such as those disclosed in U.S. Pat. No. 5,408,002, substrates such as those disclosed in U.S. Pat. No. 5,292,514, and graft copolymers and articles prepared therefrom such as those disclosed in U.S. Pat. Nos. 5,013,795 and 5,262,484. All of these patents and publications are incorporated by reference herein.

The biologically active substance used to derivatize the azlactone-functional support via covalent coupling can interact directly with the specific whole cell population intended to be selected. Nonlimiting examples of such substances include an antibody (Ab) directed toward a specific cell surface marker (or antigen, Ag) expressed on the surface of the whole cell to be selected. Alternatively, the biologically active substance may interact with the selected whole cell population through a second, intermediary biologically active substance.

A feature of the present invention is the ease of preparation of supports useful for whole cell selection.

Another feature of the present invention is the versatility and variety of methods available for the preparation of azlactone-functional supports that can be modified to be useful for whole cell selection.

Another feature of the present invention is that the surface characteristics of the whole cell selection supports can be readily controlled to minimize or prevent nonspecific interactions with non-target whole cells.

An advantage of the invention is that target whole cell populations may be isolated which have higher purities than those isolated using conventional supports, such as those identified above in the Background of the Invention that utilize chemistries other than azlactone chemistry.

Another advantage of the present invention is that target whole cell populations may be isolated in higher yields than those isolated using conventional supports and in a manner that retains biologically activity.

Further features and advantages are disclosed in the following embodiments of the invention.

EMBODIMENTS OF INVENTION

Azlactone-functional Supports

Azlactone-functional supports can be any compound or material containing or comprising at least one azlactone moiety that can be derivatized by covalent reaction with a biologically active substance. Such azlactone-functional supports are well known in the art. Preferably, the azlactone-functional support is a solid, insoluble material, wherein the term "insoluble" means does not dissolve in the medium from which the whole cell selection is to take place, comprising azlactone moieties on its surface which are readily available for reaction with the biologically active substance useful for whole cell selection.

Nonlimiting examples of azlactone-functional supports include beads, particulates, membranes, woven and nonwoven webs, and solid plastic articles comprising azlactone moieties on their surfaces. Such types of azlactone-functional supports are variously disclosed in the collection of U.S. Patents incorporated by reference above, all of which are owned by Minnesota Mining and Manufacturing Company (3M) of St. Paul, Minn., USA.

More particularly, beaded and particulate azlactone-functional supports are extensively described in U.S. Pat. No. 5,403,902 (Heilmann, et al.) incorporated by reference herein. These supports are prepared by reverse phase suspension polymerization processes and by dispersion polymerization processes from 2-alkenyl azlactone monomers and, optionally, comonomers and crosslinkers.

Porous azlactone-functional supports, such as membranes and nonwoven materials, are described in U.S. Pat. No. 5,344,701 (Gagnon, et al.) incorporated by reference herein. These supports are prepared by graft polymerization of azlactone monomers and, optionally, comonomers to the surfaces of preexisting supports using high-energy radiation. Alternatively, azlactone monomers, crosslinkers, and optionally comonomers are coated on the surfaces of the preexisting supports, then polymerized to produce the azlactone-functional supports.

Other porous azlactone-functional supports are described in PCT Patent Publication WO 93/06925 (Rasmussen, et al.) and copending, coassigned, U.S. patent appln. Ser. No. 08/776,601, incorporated herein by reference, in which azlactone-functional particles are incorporated into a continuous porous matrix such as a fibrillated polytetrafluoroethylene membrane or a nonwoven web.

Azlactone-functional membranes prepared by solvent phase inversion techniques are described in U.S. Pat. No. 5,510,421 (Dennison, et al.) incorporated by reference herein.

Thermoplastic azlactone-functional graft copolymers and copolymer blends are described in U.S. Pat. Nos. 5,013,795; 5,262,484; and 5,408,002 (all Coleman, et al.) incorporated herein by reference. These compositions are useful for the preparation of azlactone-functional molded plastic articles such as microtitration wells and plates, petri dishes, tubing, body implants, test tubes, centrifuge tubes, beakers, cuvettes, etc., which are also useful as substrates for the preparation of supports for whole cell selection in accordance with this invention.

Other azlactone-functional substrates useful in this invention are those disclosed in U.S. Pat. No. 5,292,514 (Capecchi, et al.) incorporated by reference herein.

Biologically Active Substances

Biologically active substances useful for the present invention can interact with the target whole cells either directly or indirectly, i.e. through the intermediacy of one or more secondary biologically active substances.

Biologically active substances capable of direct interaction with target whole cells include, but are not limited to, antibodies to whole cell surface antigens, lectins, and other proteins known to interact with whole cell surfaces. A wide variety of specific whole cell surface antigens have been identified, commonly referred to as CD antigens ("Cell Separation Methods and Applications", D. Recktenwald and A. Radbruch, Eds., Marcel Dekker, NY, N.Y., 1997, pp. 297–319). It is well within the capability of one skilled in the art to prepare antibodies to these antigens. In fact, many such antibodies are currently available from commercial sources such as R&D Systems, Minneapolis, Minn., and Boehringer Mannheim Corp., Indianapolis, Ind. Covalent coupling of these antibodies to azlactone-functional supports produces supports capable of direct interaction and selection of target whole cells via antibody-antigen bonding interactions.

Other biologically active substances immobilized on azlactone-functional supports can interact with target whole cells indirectly. For example, it is within the scope of the invention to use an intermediary biologically active substance which is minimally "bifunctional", i.e. it has functionality which exhibits a specific recognition or interaction with the target whole cell population but also has a second functionality which interacts and bonds to the biologically active substance which is coupled to the azlactone-functional support. An example of such an intermediary substance would be an antibody to a whole cell surface antigen conjugated to an antigen that specifically interacts with a second antibody immobilized on the support. Another example, and a preferred intermediary for use in this invention, is an anti-CD34+ antibody conjugated to biotin. Whole cell selection is accomplished via interaction of the antibody portion with the target whole cell and of biotin with avidin immobilized on the support.

Methods of Derivatizing Supports

Methods for the immobilization of biologically active substances on azlactone-functional supports are well known in the art, and are described in detail in the above mentioned patent references. Improved immobilization conditions for proteins and antibodies, specifically, are taught in U.S. Pat. No. 5,200,471 (Coleman, et al.) and in PCT Patent Publication WO 94/22918 (Velander, et al.) and companion copending, coassigned, U.S. patent appln. Ser. No. 08/296,588 (all incorporated herein by reference). Additionally, U.S. Pat. No. 5,561,097 (Gleason, et al.), incorporated by reference, describes techniques for controlling density of ligands coupled to azlactone-functional supports.

Usefulness of the Invention

The versatility and simplicity of immobilization conditions, together with the variety of techniques available for the preparation of azlactone-functional supports, allows the preparation and optimization of whole cell selection supports to a degree previously unknown. For example, once a whole cell mixture has been identified from which a target whole cell population is desired to be selected (e.g., bone marrow or peripheral blood), a base polymer support can be identified which exhibits minimal nonspecific binding of whole cells from that mixture. This ensures a high degree of purity in the selected whole cell population. Next, an azlactone moiety can be incorporated into the base polymer support by a variety of techniques disclosed in the patent references above to provide the active chemistry needed to covalently couple the biologically active substance to the support. Finally, an appropriate biologically active substance can be immobilized on the support to provide the whole cell selection support. Depending on the identity of the biologically active substance and the specific characteristics of the target whole cells, the amount of azlactone functionality and the amount of biologically active substance incorporated can be easily optimized by one skilled in the art within routine experimentation to produce the best whole cell selection. In addition, because of the unique characteristics of azlactone coupling chemistry, the surface characteristics of the final whole cell selection support can be manipulated during the immobilization process to further optimize the whole cell selection properties of said support. In many instances, whole cell selection supports can be prepared which provide selected whole cell populations with improved purities and separation yields as compared to those obtained using conventional supports employing polyacrylamide or polystyrene polymers or conventional binding chemistries such as cyanogen bromide or carbodiimide-based coupling.

Further advantages of this invention are illustrated by the following examples, but the particular materials and amounts thereof recited in these examples, as well as other conditions and details, should not be construed to unduly limit this invention.

EXAMPLES

Test Methods

Whole cell selection/purification: Evaluation of the interaction of whole cells with particulate supports in the following examples was conducted using the Ceprate™ LC Avidin Column Kit (CellPro, Inc., Bothell, Wash.) according to the manufacturer's instructions. Selection for CD34+ whole cells was accomplished using an anti-human CD34 biotinylated monoclonal antibody (mouse) (CellPro, Inc).

Avidin coupling densities: The density of avidin coupled to azlactone supports was evaluated utilizing a biotin-p-nitrophenyl ester reagent and protocol described by Hermanson, et al., *American Biotechnology Laboratory*, September 1994, pp. 86–88.

Example 1

Evaluation of Nonspecific Binding with Ficolled Buffy Coat

Crosslinked supports were prepared according to the teachings of U.S. Pat. No. 5,403,902, by reverse-phase suspension polymerization, using the polymeric stabilizer of Example 24E of that reference. Methylenebisacrylamide (MBA) was used as crosslinker, and comonomers used were dimethylacrylamide (DMAm), acrylamide (Am), vinyldimethylazlactone (VDM), or N-acryloyl-2-methylalanine (sodium salt) (AMA). These particulate supports were elutriated to remove small particles, then packed into the Ceprate LC column for evaluation. Each column was challenged with a minimum of $50 \times 10^6$ whole cells of ficolled buffy coat, derived from fresh whole blood; the flow-through fractions were collected. Whole cell counts, for both lymphocytes and monocytes, were measured by fluorescence-activated cell sorting (FACS) and compared to those of the starting sample. Table 1 lists supports evaluated, whole cell recoveries, and nonspecific binding characteristics of the avidinated polyacrylamide support provided with the commercial kit.

TABLE 1

Supports Evaluated and % Cells Recovered

| Sample | % W/W | Monomers | % Lymphocytes | % Monocytes |
|---|---|---|---|---|
| 1a | 12.5:87.5 | MBA/DMAm | 74 | 67 |
| 1b | 25:75 | MBA/DMAm | 97 | 87 |
| 1c | 50:50 | MBA/DMAm | 93 | 83 |
| 1d | 100 | MBA | 71 | 41 |
| 1e | 10:20:70 | MBA/VDM(hydrolyzed)/DMAm | 95 | 68 |
| 1f | 10:20:70 | MBA/AMA/DMAm | 25 | 17 |
| 1g | 10:20:70 | MBA/VDM(hydrolyzed)/Am | 93 | 52 |
| 1h | 10:20:70 | MBA/AMA/Am | 79 | 46 |
| Control | [commercial polyacrylamide support (MBA/Am copolymer)] | | 91 | 81 |

Discussion: This example indicates that several monomer combinations exhibit low nonspecific binding characteristics towards lymphocytes, which would be an important characteristic for a support designed for whole stem cell selection/purification. Poorer recovery of monocytes is not a concern, and may in fact be an advantage over the commercial support, since monocyte populations include T-cells which provide antibody-mediated immunity which one would like to minimize in the preparation of cell-mediated immune cells, such as pluripotent stem cells. Additional comment need be made concerning samples 1e/1f and 1g/1h. VDM (hydrolyzed) and AMA have the identical chemical formula, however were incorporated into the resultant polymer pairs by different processes. In the case of 1e, for example, the polymer was prepared by Process II of above cited U.S. Pat. No. 5,403,902 in which VDM monomer was copolymerized, then the resultant support was hydrolyzed to produce the test sample. Sample 1f, on the other hand, was prepared by copolymerization of AMA, the synthetic precursor of VDM. Thus, the method of preparation of a polymer can influence its interaction with biological species, even though it presumably has the same chemical formulation.

Example 2

Evaluation of Nonspecific Binding from Mobilized Peripheral Blood

The best performing supports from Example 1, as well as support 1f, were evaluated as in Example 1 except that the challenge was mobilized peripheral blood to which the anti-CD34+ antibody had been added prior to addition to the column. Results are listed in Table 2.

TABLE 2

Cell Recovery from Mobilized Peripheral Blood

| Sample | % Lymphocytes | % Monocytes | % Overall Cell Recovery |
|---|---|---|---|
| 1a | 87 | 100 | 89 |
| 1b | 98 | 88 | 93 |
| 1c | 91 | 83 | 87 |
| 1d | 62 | 29 | 52 |
| 1e | 91 | 90 | 88 |
| control | 90 | 85 | 87 |

This example also illustrates that it is possible to find polymer backbones that exhibit equivalent or lower nonspecific binding as compared to the prior art.

Example 3

Azlactone/Dimethylacrylamide Supports

Particulate supports were prepared from MBA, VDM, and DMAm by reverse phase suspension polymerizations according to Process II of U.S. Pat. No. 5,403,902. In these experiments, total weight of monomers was 20 g. The MBA and DMAm monomers were dissolved in a mixture of methanol (30 ml) and water (70 ml). After dissolution, sodium persulfate (0.5 g) was added and allowed to dissolve. This solution was then added to a stirring solution, under nitrogen, of VDM, toluene (132 ml), heptane (243 ml), and stabilizer (0.33 g) pre-equilibrated to 35° C. The nitrogen purge was continued for 5 minutes, then tetramethylethylenediamine (TMEDA, 0.5 ml) was added to initiate the polymerization. Polymerization was continued for 2 hours, the product was collected by filtration, washed with acetone, elutriated using methanol as liquid phase to remove particles smaller than 100 microns in diameter, and dried under vacuum to constant weight. Avidin coupling: Avidin was coupled to the supports using a solution of avidin (1 mg/ml) in 0.1 M sodium carbonate/1.4 M sodium sulfate buffer, pH 9.5. After coupling, excess azlactone functionality was quenched using 0.2 M glycine, pH 9.0. Each support was evaluated in duplicate for selection of CD34+ whole cells. Each Ceprate LC column of support (2.0 ml) received a total of $2.0 \times 10^8$ whole cells from a fresh marrow sample. Table 3 lists support composition, number and % yield of target whole cells selected (averages of duplicates).

TABLE 3

Whole cell Selection with VDM/DMAm Supports

| Sample | Composition | | CD34 + Whole Cells | % Yield |
|---|---|---|---|---|
| 3a | 10:20:70 | MBA/VDM/DMAm | $0.59 \times 10^6$ | 32.6 |
| 3b | 20:20:60 | MBA/VDM/DMAm | $1.01 \times 10^6$ | 55.7 |
| 3c | 47:6:47 | MBA/VDM/DMAm | $1.24 \times 10^6$ | 68.7 |
| control | | | $1.05 \times 10^6$ | 58.4 |

Example 4

Azlactone/Acrylamide Supports

Supports were prepared as in Example 3 substituting acrylamide for dimethylacrylamide, and were evaluated as in Example 3. Results are listed in Table 4. %Yields are shown relative to that of the control for CD34+ whole cells.

TABLE 4

Whole cell Selection with VDM/Am Supports

| Sample | Composition | Avidin Density (μ/ml) | % Yield |
|---|---|---|---|
| 4a | 5:20:75 MBA/VDM/Am | 45 | 94 |
| 4b | 10:20:70 MBA/VDM/Am | 66 | 120 |
| 4c | 20:20:60 MBA/VDM/Am | 59 | 101 |
| control | | 1000 | 100 |

Discussion: Examples 3 and 4 illustrate that excellent whole cell selection can be obtained with azlactone-based supports.

Example 5

Avidin Density Study

A 20:20:60 MBA/VDM/DMAm support similar to Example 3b was prepared. Samples of support were challenged with varying concentrations of avidin in order to provide a range of avidin coupling densities. Supports were evaluated as in Example 3; results are shown in Table 5, with %yield reported as relative to the commercial control.

TABLE 5

Whole cell Selection vs. Avidin Density

| Sample | Avidin Density (μg/ml) | % Yield |
|---|---|---|
| 5a | 80 | 39 |
| 5b | 101 | 48 |
| 5c | 190 | 90 |
| 5d | 775 | 96 |
| 5e | 1414 | 112 |
| control | 1000 | 100 |

These data, along with those of Example 4, indicate that supports prepared from azlactone-functional particles perform comparably to conventional supports, but can do so at much lower avidin density levels.

Example 6

A 20:20:60 MBA/VDM/DMAm support was prepared by the two-step procedure of Process I of U.S. Pat. No. 5,403,902. After drying, this support was classified using a Sonic Sifter (ATM Corporation, Milwaukee, Wis.) to provide two size cuts 6a (106–150 microns) and 8b (75–106 microns). Upon hydration, sample 6a measured 204 microns average diameter while 6b measured 155 microns. Avidin was coupled using 0.1 M carbonate buffer, pH 9.5 under a variety of conditions, then the supports were evaluated for CD34+ selection using marrow and mobilized peripheral blood samples. Coupling conditions: (a) 1 mg/ml avidin, 1.4 M sulfate; (b) 1 mg/ml avidin, no sulfate; (c) 4 mg/ml avidin, 1.4 M sulfate; (d) 3 mg/ml avidin, no sulfate. Results are listed in Table 6, with % purities and yields normalized to those of the control support.

TABLE 6

Whole cell Selection with VDM/DMAm Supports Prepared by Process I

| Sample | Coupling Condition | Avidin Density (μg/ml) | % Yield | % Purity |
|---|---|---|---|---|
| Tested with Mobilized Peripheral Blood | | | | |
| 6a | a | 93 | 94 | 67 |
| 6a | b | 1282 | 71 | 66 |
| 6b | b | 1396 | 115 | 92 |
| 6a | c | 126 | 98 | 73 |
| 6a | d | 1432 | 95 | 91 |
| 6b | d | 1454 | 110 | 100 |
| Tested with Marrow | | | | |
| 6a | c | 126 | 115 | 100 |
| 6a | d | 1432 | 113 | 106 |
| 6b | d | 1454 | 121 | 108 |

This example produced a number of surprising results: (1) The density of coupled avidin was found to be much higher in the absence of sulfate than in its presence, a result which was also verified with the supports above prepared according to Process II. This is in sharp contrast to prior art that showed increased protein coupling efficiencies to azlactone-functional supports in the presence of sulfate (U.S. Pat. No. 5,200,471 (Coleman et al.)). (2) Process I supports exhibited improved % yield performance over Process II beads, despite being of the same chemical composition (see Example 4c). (3) Process I beads also exhibited exceptional purities as compared to the control support. (4) Optimum performance with azlactone-functional supports occurs with a much smaller particle than with the control support, a 250-micron bead.

Example 7

The support synthesis described in Example 6 was repeated except that polymerization was conducted using sodium persulfate as the only initiator and the reaction temperature was 55° C. The classified sample exhibited a hydrated mean size of 214 microns. Avidin was coupled at a density of 307 μg/ml and evaluated as before, giving comparable yields and improved purities as compared to the control support.

Example 8

A support was prepared as in Example 7, and coupled to NeutraAvidin™ (Pierce Chemical, Rockford, Ill.) at a density of 70 μg/ml. When evaluated for CD34+ selection from marrow, this support exhibited 108% purity and 129% yield as compared to the control support.

Example 9

Microtitration plates having azlactone groups on the interior surfaces of the wells are molded from (a) the polymethylmethacrylate/polyVDM blend prepared according to Example 28 of U.S. Pat. No. 5,408,002 and (b) the VDM-grafted polypropylene prepared according to Example 44 of U.S. Pat. No. 5,262,484. Using the protocol for whole cell "panning" in Esser, in "Cell Separation Methods and Applications", D. Recktenwald and A. Radbruch, Eds., Marcel Dekker, NY, N.Y., 1997, p. 8, excellent whole cell selection is achieved as compared to that using non-azlactone functional control plates.

Example 10

An azlactone-functional nonwoven pad was prepared according to Example 20 of U.S. Pat. No. 5,344,701. Derivatization with an anti-CD4 antibody as described in Pope, et al., *Bioconjugate Chem.,* 1993, 4, pp. 166–171 allows facile depletion of CD4+ mononuclear whole cells from a peripheral blood sample in a simple flow-through filtration mode. The porosity of the nonwoven allows unbound whole cells to easily flow through the construction, while the immobilized antibody captures the CD4+ whole cells.

Alternatively, azlactone-functional membranes can be made according to U.S. Pat. No. 5,510,421, derivatized with an appropriate antibody, and used for whole cell selection in a crossflow filtration mode.

Example 11

The Use of Azlactone-functional Beads to Type Human Blood Cells

Commercially available anti-sera selective for blood groups A and B is incubated with Protein A-derivatized azlactone beads (prepared according to Example 4 of U.S. Pat. No. 5,200,471) in phosphate-buffered saline (PBS) at a ratio of about 5 mg of serum IgG to 1 mL of packed beads by rocking at ambient temperature for about 15 minutes. Unbound protein is removed by multiple rinsing steps using PBS and centrifugation. A sample of human blood is diluted with PBS ten-fold. 200 $\mu$L samples of the diluted blood are incubated with about 50 $\mu$L each of the above anti-sera-Protein A-azlactone bead preparation at ambient temperature with gentle mixing for about 15 min. The beads are allowed to settle for several minutes, then the turbidity of the supernatant liquid is compared with that of controls in which the Protein A beads were incubated with pre-immune serum. The control samples are turbid because no blood cells settle with the beads to the bottom of the tube. The tubes containing cells of the same blood type as the anti-serum are clear or greatly reduced in turbidity compared with the controls.

Example 12

Typing Hman Blood Through Direct Immobilization of a Specific Antibody.

Antibodies to human blood group antigens or any other cell surface marker may be immobilized directly onto azlactone-functional supports and used for blood typing (as described in Example 11) or for purification of a particular fraction of whole cells. To remove the specifically bound whole cells incubate the specific antigen with the bead-antibody-whole cell suspension after washing away the unbound whole cells with several rinses of isotonic buffer. For example, for release of selected whole cells of blood group A, dilute the suspension to approximately 0.1 mL of beads per mL of suspension containing 1 mg/mL or greater concentration of the required antigen. For example, blood group A positive whole cells may be eluted using a short polysaccharide terminating in alpha-N-Ac-galactosamine. Other antigens would need to be specific to the expressed markers on the captured whole cell surface.

Example 13

Direct Immobilization of Whole Cells to Select Specific Whole Cells That Bind to Them Activated T-cell lymphocytes presenting cell surface marker CD-28 can be purified from a population of lymphocytes (e.g., a buffy coat fraction from a whole blood sample) by their ability to bind to antigen-presenting cells or macrophages. Purified antigen presenting cells can be immobilized directly to azlactone-functional supports by incubation (with gentle agitation for about 15 minutes) of about 1 million whole cells with 1–2 mL of beads in an isotonic buffer that is substantially free of primary amine. Uncoupled whole cells are removed by settling the suspension, removing the supernatant solution, and several rinses. 1 mL of the immobilized antigen presenting cell preparation is incubated with about 10 mL of a buffy coat preparation that has been diluted with PBS to about 0.5 million whole cells/mL for 30 min with gentle rocking. The support is allowed to settle, the supernatant solution is removed, then two wash steps with five volumes of PBS are conducted. Purified T-whole cells may be removed by gentle stirring of the bead slurry while flowing PBS through the slurry (such as by using the Ceprate device).

The invention is not limited by the embodiments described above. The following claims are made.

What is claimed is:

1. A method for cell selection comprising:
   (a) prescreening base polymer supports with a whole cell mixture to identify one or more base polymer supports that exhibit minimal nonspecific binding of whole cells from the mixture,
   (b) incorporating an azlactone moiety into the one or more base polymer supports identified in step (a) to provide an azlactone-functional support,
   (c) derivatizing the azlactone-functional support with a substance that is biologically active with a desired type of whole cell, wherein the substance is covalently coupled to the azlactone-functional support,
   (d) contacting the product of step (c) with the whole cell mixture,
   (e) allowing the whole cells to interact with and bind to the coupled biologically active substance, and
   (f) removing a remainder of the mixture from the support.

2. The method of claim 1, wherein the azlactone-functional support is a support having a surface comprising azlactone moieties and is selected from the group consisting of a bead, a particulate, a membrane, a blended article, a graft copolymeric article, a woven web, a nonwoven web, a solid plastic article, and combinations thereof.

3. The method of claim 1, wherein the biologically active substance is selected from the group consisting of antibodies, lectins, proteins, antigens, avidin, and combinations thereof.

4. The method of claim 1, wherein the biologically active substance directly interacts with the whole cells.

5. The method of claim 1, wherein the biologically active substance indirectly interacts with the whole cells through a second, intermediary biologically active substance that is bifunctional to both the whole cells and the azlactone-functional support.

6. The method of claim 1, wherein the azlactone-functional support is prepared by processes selected from the group consisting of suspension polymerization processes and dispersion polymerization processes.

7. The method of claim 6, wherein the azlactone-functional support is prepared from 2-alkenyl azlactone monomers.

8. The method of claim 2, wherein the solid plastic article is a microtitration well, a microtitration plate, a petri dish, medical tubing, a test tube, a centrifuge tube, a beaker, a cuvette, or a body implant.

9. The method of claim 1, further comprising the step of eluting the bound cells from the coupled biologically active substance to provide a purified collection of whole cells.

10. The method of claim 1, wherein the mixture is selected from the group consisting of bone marrow and peripheral blood.

11. The method of claim 7 wherein the azlactone-functional support is prepared from comonomers.

12. The method of claim 7 wherein the azlactone-functional support is prepared from crosslinkers.

* * * * *